US006539775B2

(12) United States Patent
Driftmeier

(10) Patent No.: US 6,539,775 B2
(45) Date of Patent: Apr. 1, 2003

(54) METHOD AND APPARATUS FOR THE MEASUREMENT OF THE INTERCHANGEABILITY OF LPG/AIR MIXTURES WITH NATURAL GAS

(76) Inventor: Wolfgang H. Driftmeier, 2409 Walker Dr., Lawrenceville, GA (US) 30043

( * ) Notice: Subject to any disclaimer, the term of this patent is extended or adjusted under 35 U.S.C. 154(b) by 0 days.

(21) Appl. No.: 09/781,213

(22) Filed: Feb. 13, 2001

(65) Prior Publication Data

US 2002/0108430 A1 Aug. 15, 2002

(51) Int. Cl.[7] .............................................. G01N 9/00
(52) U.S. Cl. ........................ 73/23.2; 73/30.01; 702/24
(58) Field of Search .............................. 73/23.2, 30.01, 73/30.02; 702/24, 30

(56) References Cited

U.S. PATENT DOCUMENTS

| | | | | |
|---|---|---|---|---|
| 4,941,345 | A | * | 7/1990 | Altemark et al. ............. 73/23.2 |
| 5,635,626 | A | * | 6/1997 | Hammond et al. ............ 137/79 |
| 5,822,058 | A | * | 10/1998 | Adler-Golden et al. ...... 356/300 |
| 6,058,761 | A | * | 5/2000 | Vander Heyden .......... 73/30.01 |
| 6,279,380 | B1 | * | 8/2001 | Van Wesenbeeck et al. ...... 73/23.31 |

FOREIGN PATENT DOCUMENTS

GB 2333371 A * 7/1999

* cited by examiner

Primary Examiner—Daniel S. Larkin
Assistant Examiner—Michael Cygan

(57) ABSTRACT

An apparatus for the continuous measurement of the interchangeability of LPG/Air Mixtures with Natural Gas, having a sensor that measures the relative density (specific gravity) of an LPG/air mixture, and associated controls for gas sampling, signal processing and computation of mixture properties and interchangeability factors. The entire apparatus, gas sampling components, and signal conditioning devices are carried in one or more housings, having one sample gas inlet port and one or more waste gas outlet ports, one gas density sensor, one or more microprocessor-based signal processing units, and one or more connected operator interfaces. The measurement data from the gas density sensor is combined in the microprocessor-based signal processing unit with user-provided information about the properties of the LPG feedstock. The microprocessor-based signal processing unit applies a series of computations to the raw measurement data and displays the results on the operator interface in one or more user-selectable engineering units. The results of the computation allows the user to determine whether the LPG/Air mixture is suitable to replace natural gas in standby, backup, peak shaving and natural gas stabilization systems.

5 Claims, 1 Drawing Sheet

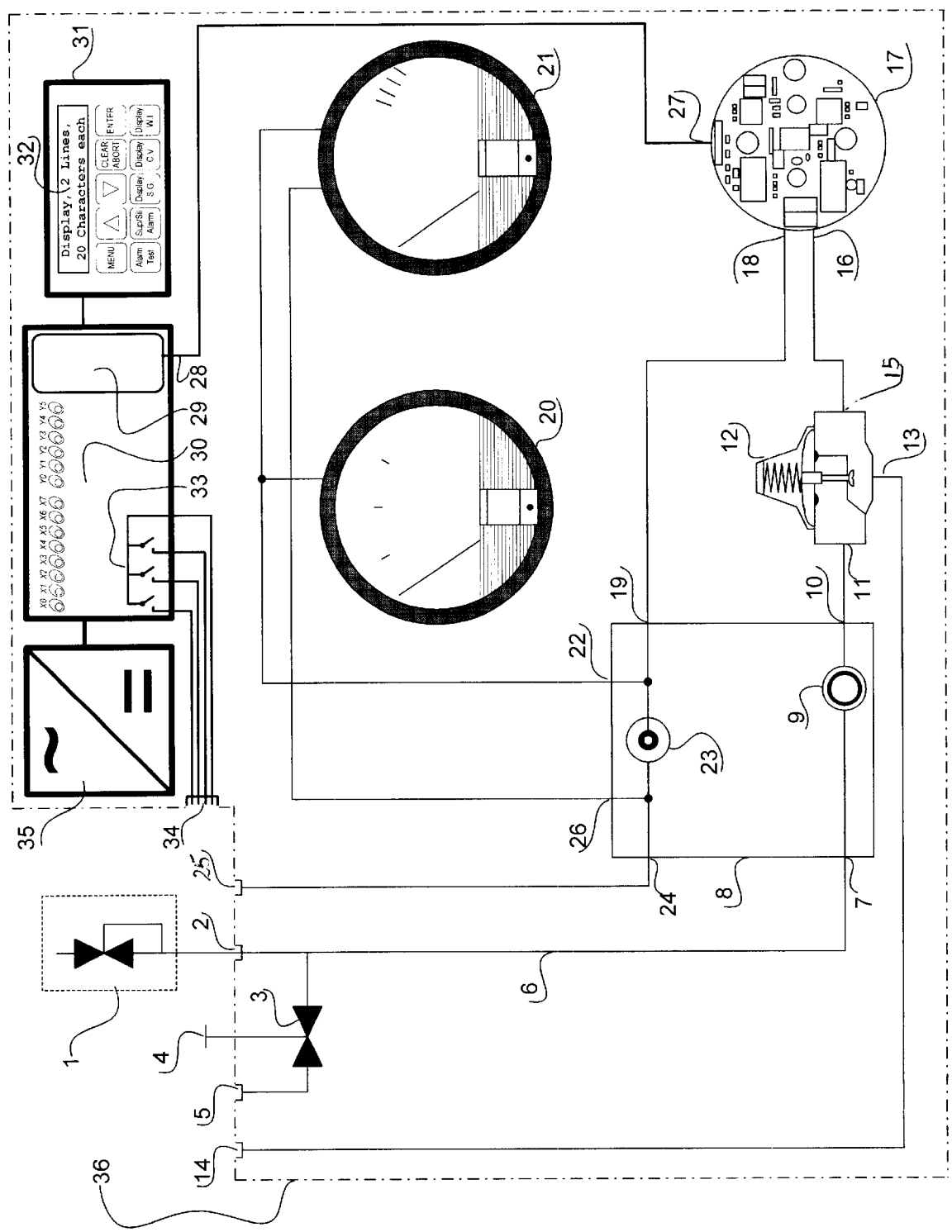

METHOD AND APPARATUS FOR THE MEASUREMENT OF THE INTERCHANGEABILITY OF LPG/AIR MIXTURES WITH NATURAL GAS

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

1. Technical Field

This invention relates to an apparatus and method for the measurement of the interchangeability of LPG/air mixtures with natural gas, as used in standby, backup, or peak shaving systems. The invention offers a user a direct readout of a commonly accepted interchangeability factor (Wobbe Index).

2. Description of the Background Art

Control and reporting for combustible gases such as natural gases or industrial gas mixtures is necessary to assure the quality and usefulness of the gas to a user. While this is sometimes accomplished using composition analysis such as from a gas chromatography and by other methods, these methods are typically slow, and the associated instrumentation is expensive to purchase, operate, and to maintain. Natural gas, primarily methane with dilute mixtures of other gases, is a preferred fuel for energy generation or heat generation because it is clean and efficient.

In many countries, gas for use in households and industries is not available from long distance natural gas pipelines. In these instances, industrially produced gases such as propane and butane are mixed for distribution in local distribution systems. In some cases, natural gas is available, but in limited supply. Mixtures of propane and butane ("LPG") are then used for peak shaving of the natural gas supply. In still other situations, gas, which is represented to be propane, contains butane in some amount. In order to use such industrially produced gases for residential and industrial fuel, it is necessary that the composition of the gas be controlled. This is accomplished by measuring the relative density and/or the calorific value of the mixed gases, and controlling the proportion of air in the mixture to adjust the properties of the overall mixture. This prevents the gas from being supplied to customers in a mixture that is too rich or too lean.

In such blending systems, mixing to a consistent Wobbe Index (the ratio of heating value to the square root of relative density) is the operating goal. When the supply gas relative density, and the properties of the LPG feedstock are known, relative density of the mixed gas and its heating value are sufficiently related to make it possible to control the blending of the product using only the relative density measurement.

The measurement of the relative density of gases has been carried out using several methods and instruments. One instrument has a construction similar to a laboratory balance for measuring a ratio of the weight of a sample gas to the weight of air. The relative density of gases is related to air, which is assigned a relative density of 1.0.

Another device for measuring relative density spins a volume of gas and a volume of air in sequential fashion and measures the weight in known volumes. Spinning enhances the sensitivity of the instrument since rotational acceleration increases the forces involved in the weight measurement.

Neither method allows the user to determine whether the mixed gas is indeed interchangeable, and/or compatible with, the natural gas it is to replace, as these methods deliver only one part of the information necessary to compute the interchangeability factor (Wobbe Index), and secondary operations would be required to complete the decision-making process.

BRIEF SUMMARY OF THE INVENTION

The invention relates to apparatus and methods for determining the interchangeability factor of gases such as propane and butane alone or mixed together and mixed with air in a system utilizing low or high pressures.

The invention measures relative density using a gas density sensor, and processes the density signal together with pre-defined or user-definable information about the LPG mixture. The result from the signal processing is presented as the Wobbe Index of the mixed fuel gas. The result can be presented in any required engineering unit, typically. BTU/cuft, or J/m3.

In the method of this invention, the relative density signal, when combined with information about the LPG mixture, is a linear function of the Wobbe index.

Accordingly, it is an object of the present invention to provide a method and apparatus for determining the interchangeability of LPG/air mixtures with natural gas which is easy to use, reliable, less expensive to manufacture and to operate than systems of the prior art, and efficient in operation.

Another object of the present invention is to provide a method and apparatus for use with various types of LPG mixtures.

Another object of the present invention is to provide the user with increased flexibility to adapt the apparatus to various operating conditions.

Another object of the present invention is to provide an apparatus, which utilizes a minimum of moving parts and requires low maintenance.

Another object of the present invention is to provide a method that allows continuous, on-line measurement and real-time display of the interchangeability factor "Wobbe Index".

Another object of the present invention is to provide an apparatus, which can be housed in a single enclosure, making it suitable for installations with limited space availability.

Another object of the present invention is to provide an apparatus, which can be assembled in such a way that its electrical components can be housed in an explosion-proof enclosure, making the apparatus suitable for hazardous locations.

Other objects and advantages, besides those discussed above will be apparent to those of ordinary skill in the art from the description of the preferred embodiment, which follows. In the description, reference is made to the accompanying drawing, which forms a part hereof, and which illustrates examples of the invention. Such examples,

BRIEF DESCRIPTION OF THE DRAWING

FIG. 1 is a block diagram of an apparatus for practicing the method of the present invention.

DETAILED DESCRIPTION OF THE INVENTION

Referring to FIG. 1, a first embodiment of an apparatus for practicing the method of the invention uses a first level pressure regulator 1 to supply a continuous sample of the mixed fuel gas to the sample gas port 2. A bypass valve 3, which is operated by means of a manual lever 4, increases flow (and, thereby, response time) during initial setup of the LPG/air mixing system. Excess sample gas exits the apparatus at the bypass valve waste port 5.

The sample gas line 6 is connected to the inlet port 7 of a multi-function manifold block 8, which includes an integral filter device 9 for the purpose of removing solid particles in the fuel gas sample.

The fuel gas sample exits the multi-function manifold block 8 at the sample gas outlet port 10 and is routed to the inlet port 11 of the secondary pressure regulator 12, where its pressure is further reduced. The secondary pressure regulator 12 vents excess sample gas through its vent port 13, which is connected to the regulator vent port 14.

The regulator outlet port 15 is connected to the sample gas inlet port 16 of the gas density sensor 17.

After leaving the density sensor through its sample gas outlet port 18, the fuel gas sample enters the multi-function manifold block 8 at the return line inlet 19.

A pressure gauge 20, and one side of a differential pressure gauge 21, is connected to the multi-function manifold block 8 at the pressure port 22, which is internally connected to the return line inlet 19.

The return line inlet 19 is further internally connected to the inlet side of a consumption jet 23. The orifice size of the consumption jet 23 determines the maximum flow of sample fuel gas through the gas density sensor 17.

The outlet side of the consumption jet 23 is internally connected to the outlet port 24 of the multi-function manifold block 8, and to the waste gas port 25 of the system.

The outlet port 24 of the multi-function manifold block 8 is further internally connected to the differential pressure port 26, which is connected to the reference side of the differential pressure gauge 21.

The pressure gauge 20 is used to indicate the sample gas supply pressure to the gas density sensor 17. The differential pressure gauge 21 would indicate an above-zero pressure under normal operating conditions, and zero pressure if the consumption jet 23 were blocked.

Filter device 9 and consumption jet 23 are equipped with removable screw-caps, allowing easy cleaning and replacement.

The output 27 of the gas density sensor 17 is electrically connected to the inlet port 28 of the analog module 29 of the signal processor 30.

The signal processor 30 processes the density information together with user-provided information about the properties of the LPG and displays the results (Wobbe Index, Calorific Value, Specific Gravity) at the display 31 of the operator interface 32.

The operator interface 32 is also used to load LPG specific information, as well as desired min/max monitoring ranges, into the signal processor 30.

The signal processor also compares the results of the processing against user-definable setpoints, and activates one or more alarm contacts 33, which are connected to externally available terminals 34, if the results are outside desired limits.

The signal processor can also produce an analog or digital output signal that can be used by external components to correct the LPG/air mixture to maintain a desired Wobbe Index.

Gas density sensor 17, signal processor 30, and operator interface 32 are supplied with electric energy through a power supply 35, which shares the enclosure 36 with items 2 to 34.

This has been a description of examples of how the invention can be carried out. Those of ordinary skill in the art will recognize that various details may be modified in arriving at other detailed embodiments, and these embodiments will come within the scope of the invention.

I claim:

1. A method for determining the interchangeability factor of LPG/air mixtures with natural gas, the method comprising:

using the electrical output signal from a gas density sensor and processing this signal together with user-supplied information about the LPG feedstock to calculate the Wobbe Index of the LPG/air mixture;

offering the user a list of pre-defined LPG (propane/butane) mixtures with associated gas properties for LPG feedstock selection;

offering the user the option to create a new LPG (propane/butane) mixture with automatic computation of the resulting gas properties for this new LPG feedstock;

offering the user the option to enter detailed LPG feedstock information to be used by the invention, together with the signal from the gas density sensor, for the computation of the Wobbe Index;

producing reliable, accurate, real-time information about the interchangeability of the LPG/air mixture with natural gas.

2. The method of claim 1, wherein the user can provide information about the LPG feedstock properties in several different ways.

3. The method of claim 2, wherein the information about the LPG feedstock can be entered as the selection from a list of pre-defined LPG mixtures, or as a new LPG propane/butane mixture ratio, or as mixture-specific data.

4. The method of claim 3, wherein the relevant information about the LPG mixture properties is automatically calculated based on the propane/butane mixture ratio.

5. An apparatus for determining the interchangeability of LPG/air mixtures with natural gas, the apparatus comprising: a processor which receives a linear density signal from a gas density sensor, combining this signal with user-provided information about the LPG feedstock properties, producing a processing result that is displayed in common engineering units as the interchangeability factor Wobbe Index; an operator interface to display the processing results and to enter LPG feedstock information; means for supplying sample gas at a reduced pressure to the density sensor; a multi-function manifold block with integral filter device and consumption jet; a pressure gauge to indicate sample gas pressure; a differential pressure gauge to indicate flow through the system; and a bypass valve in the sample gas line to increase flow during initial system setup, wherein the multi-function manifold block is fitted with an integral filter device and a consumption jet, reducing the number of fittings to be used in the piping assembly, and thereby reducing the risk of gas leaks, wherein the multi-function manifold block has removable screw caps for easy access to filter device and a consumption jet.

* * * * *